United States Patent
Verdirk

(10) Patent No.: US 8,161,801 B2
(45) Date of Patent: Apr. 24, 2012

(54) METHOD OF DETERMINING THE VISCOSITY OF A FLUID

(75) Inventor: Michael Verdirk, Felsberg (DE)

(73) Assignee: Grundfos Management A/S, Bjerringbro (DK)

( * ) Notice: Subject to any disclaimer, the term of this patent is extended or adjusted under 35 U.S.C. 154(b) by 384 days.

(21) Appl. No.: 12/339,824

(22) Filed: Dec. 19, 2008

(65) Prior Publication Data

US 2009/0165565 A1    Jul. 2, 2009

(30) Foreign Application Priority Data

Dec. 21, 2007   (EP) ..................................... 07024873

(51) Int. Cl.
   *G01N 11/02* (2006.01)
(52) U.S. Cl. ....................... 73/54.02; 73/54.01; 73/54.42
(58) Field of Classification Search ................. 73/54.02, 73/54.42, 54.01
   See application file for complete search history.

(56) References Cited

U.S. PATENT DOCUMENTS

| | | | | |
|---|---|---|---|---|
| 4,241,602 A | * | 12/1980 | Han et al. ..................... | 73/54.14 |
| 5,447,073 A | * | 9/1995 | Kalinoski .................. | 73/861.24 |
| 6,237,425 B1 | | 5/2001 | Watanobe | |
| 7,007,556 B2 | * | 3/2006 | Keita et al. ................. | 73/861.22 |
| 2009/0090504 A1 | * | 4/2009 | Weightman et al. ..... | 166/250.01 |

OTHER PUBLICATIONS

Boucher R. F. et al.; "Low Reynolds number fluidic flowmetering"; Journal of Physics E. Scientific Instruments; vol. 21; No. 10; pp. 977-989; Oct. (1988).

Williamson, C. H. K.; "Vortex Dynamics in the Cylinder Wake"; Annual Review Fluids Mechanics; vol. 28; pags. 477-539; (1996).

* cited by examiner

*Primary Examiner* — Hezron E Williams
*Assistant Examiner* — Paul West
(74) *Attorney, Agent, or Firm* — Panitch Schwarze Belisario & Nadel LLP

(57) ABSTRACT

A method is used to determine the viscosity of a fluid. The method includes arranging a body (11) in a fluid-leading channel, with which vortices form in the flow direction (10) therebehind, which are detected with regard to measurement technology. Also, the flow speed in the channel, at which vortices arise for the first time or barely just continue to exist, is determined, and this speed is used as a measure for the viscosity of the through-flowing fluid.

16 Claims, 3 Drawing Sheets

METHOD OF DETERMINING THE VISCOSITY OF A FLUID

BACKGROUND OF THE INVENTION

The invention relates to a method for determining the viscosity of a fluid, as well as to a device for carrying out this method.

In flow mechanics, the phenomenon with which a body is arranged within a flow and with which counter-running vortices form therebehind in the flow direction, is called a Karman vortex street. If such a body is subjected to onflow with a low speed, then the flow runs in a laminar manner with a low Reynolds number. With an increasing speed (higher Reynolds number) first, stationary vortices are formed, which given an increase of the flow speed, detach and form a so-called vortex street behind the body. The detachment frequency of the vortices may be determined by way of the Strouhal number, which is dependent on the shape of the body. On account of the linear relation of the detachment frequency and the flow speed, this physical effect is utilized for the flow measurement with non-abrasive, low viscosity media. Such measurement arrangements are known as vortex flowmeters.

Such a vortex flowmeter is for example described in European Patent Publication No. 1 434 034 A 1. Such a vortex flowmeter is particularly applied in conduit systems of circulations, be it in the conduit itself or also within the pump producing the circulation. Such a measurement arrangement typically consists of a body projecting into the flow, the body being a so-called obstruction, and of a sensor arranged at a suitable distance therebehind, typically a pressure sensor, in particular a differential pressure sensor. Such components nowadays may be manufactured in an inexpensive manner and may determine the flow rate with a high accuracy.

With such conduit circulations, as are to be found, for example, in heating systems, in solar installations, in the cooling water circulation of a vehicle or likewise, the measurement of the flow speed is often not sufficient. In modern systems, all system variables which are significant for the operation should be detected in an as continuous and reliable as possible manner. It is therefore the object of the present invention to detect a further variable which is relevant for the operation of an installation, in particular with a vortex flow measurement device with as few as possible modifications.

BRIEF SUMMARY OF THE INVENTION

This object is achieved by the features of the present invention.

The method according to the invention serves to determine the viscosity of a fluid. With the method according to the invention, a body which produces vortices when subjected to onflow is arranged in a fluid-leading channel and projects into this channel, wherein at least one vortex forming behind the body in the flow direction is detected with regard to measurement technology and the flow speed in the channel is determined at which vortices arise for the first time or just about continue to exist, wherein this flow speed which is then evaluated is utilized as a measure for the viscosity of the through-flowing fluid.

The construction for carrying out the method according to the invention, with regard to the device, envisages a measurement arrangement for integrating into a conduit, which comprises a body and a pressure sensor or preferably differential pressure sensor arranged at a distance thereto, as well as means for changing the flow speed in the conduit, and an electronic control and evaluation device with which on the one hand the flow speed in the conduit may be controlled, and with which on the other hand the evaluation of the pressure sensor signal, in particular the differential pressure sensor signal, is effected for determining the viscosity of the fluid in the conduit.

The basic concept of the present invention is thus to incorporate a further use, specifically the viscosity measurement, into a vortex measurement device. Astonishingly, it has been found that a clear dependency between the flow speed at which a vortex barely just forms behind the body, or with a reducing speed, such a vortex barely just continues to exist, represents a measure for the viscosity for the fluid flowing through, so that with a simultaneous detection of the speed, one may directly obtain information with regard to the viscosity of the fluid.

The method according to the invention may advantageously be carried out with a vortex flow measurement device, but is not limited to this, and, as the case may be, may also be used with a signal coming from another source, for the flow speed in the conduit. The method according to the invention is effected particularly advantageously in combination with a vortex measurement device, with which therefore the flow speed and the viscosity of the through-flowing medium are detected simultaneously with a measurement device. Advantageously thereby, a flow is produced with an increasing or reducing speed, in order to determine the flow speed at which vortices arise for the first time or barely just continue to exist. This point at which vortices arise for the first time (with an increasing flow speed) or barely just continue to exist (with a reducing flow speed), is determined by way of increasing or reducing speed of the flow.

Usefully, the evaluation of this speed at which vortices arise for the first time or barely just continue to exist, is effected by way of a measurement device which detects the frequency of the vortices forming behind the body in the flow direction, in the channel, and via this frequency determines the flow speed. Such frequency detection may be effected via a pressure sensor arranged there, but the frequency detection is, however, preferably effected by way of a differential pressure sensor as is typically applied in pipe conduits or pumps, arranged in the vortex region. Such differential pressure sensors are available nowadays in an inexpensive manner and are stable over long periods of time.

Apart from the detection of the frequency, advantageously, a temperature detection of the through-flowing fluid is also additionally effected, which is taken into account when determining the viscosity. Although, depending on the application, it may be sufficient to determine the viscosity by way of the flow speed at which vortices form for the first time or vortices barely just continue to exist, the detection of the temperature of the through-flowing medium is advantageous, particularly when the through-flowing speed has a changing temperature.

If the fluid, for example, consists of water and glycol, as this is often the case with heat transfer medium fluids, for example, in a motor vehicle, in solar collectors or likewise, then according to an advantageous further formation of the invention, one may determine the glycol content of the water and/or the freezing point of the fluid by way of the viscosity of the fluid, as the case may be, while taking its temperature into account. Thus, with a common vortex flowmeter, one may determine whether the antifreeze projection is adequate or not, in a simple and quick manner without intervening in the system. Glycol here is only one example of a multitude of substances which may be mixed with water or other fluids.

If, as is the rule with heat-exchanger installations, the channel is formed by a conduit impinged by a centrifugal pump, this pump may advantageously be activated with an increasing or decreasing rotational speed for determining the viscosity, which is possible without much technical effort, in particular with modern centrifugal pumps whose rotational speed may be changed.

If such an activation of the pump, for whatever reason, is not possible, then according to an alternative design of the method according to the invention, one may provide means for throttling or opening the conduit cross section, in order to determine the flow speed at which vortices arise for the first time or barely just continue to exist, and thus to detect the viscosity. The channel may then be formed by a conduit impinged by any pressure source, be it by a pressure storage means or also a centrifugal pump whose rotational speed may not be controlled, or whose control is not suitable for the method describe above.

The method according to the invention may be carried out with a suitable device whose components to a large extent are already present in known installations. Thus, a measurement arrangement provided for integration into a conduit, with a body and a differential pressure sensor arranged at a distance thereto, are often already integrated on the pump side or are present on account of a measurement module for determining the flow speed, which is integrated into the conduit. Such vortex measurement arrangements with an obstruction and a pressure sensor or differential pressure sensor arranged at a distant thereto in the flow direction, are counted as belonging to the state of the art. For changing the flow speed in the conduit, which may be typically effected by way of a suitably controllable valve arrangement or a pump which may be controlled with regard to its rotational speed, an electronic control device is typically required, which may for example be formed by a microprocessor, in which such a control function is implemented with regard to software. Moreover, an electronic evaluation device for evaluating the pressure signal or differential pressure signal for determining the flow speed and, thus, the viscosity of the fluid in the conduit is necessary, and this too may be implemented with regard to software in a simple manner in a microprocessor. The device according to the invention may therefore as a rule be constructed from components which are present in any case, or may be provided in an inexpensive manner.

Thereby, the measurement arrangement advantageously also comprises a temperature sensor, in order to increase the accuracy of the viscosity evaluation. Such temperature sensors are regularly installed in modern differential pressure sensors, and are counted as belonging to the practiced state of the art at least with a vortex measurement device.

If advantageous, a speed controllable centrifugal pump is utilized for changing the flow speed. It is then particularly advantageous if the measurement arrangement forms part of the centrifugal pump. It is then further particularly advantageous if at least a part or advantageously the complete control and evaluation electronics are arranged in the terminal box or the electronics housing of the motor of the centrifugal pump, since then the complete device may be integrated into the pump assembly, so that the device according to the invention may be integrated into an existing installation practically without additional construction measures, by way of installing a corresponding pump assembly.

If a controllable throttle valve is applied for the control of the flow speed, then the measurement arrangement may advantageously be provided within the valve arrangement, just as the control and evaluation device, so that a compact construction unit which may be handled without additional technical measures also results with this constructive alternative.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 2:
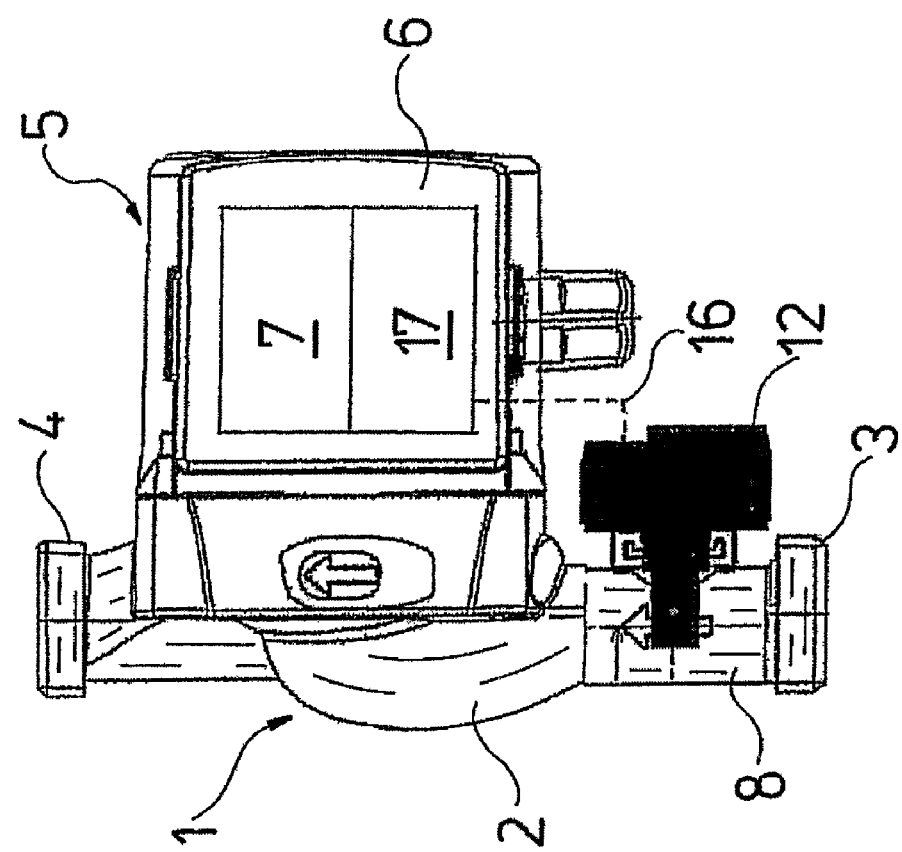
FIG. 2 is a schematic lateral view of the centrifugal pump assembly according to FIG. 1.
Figure 1:
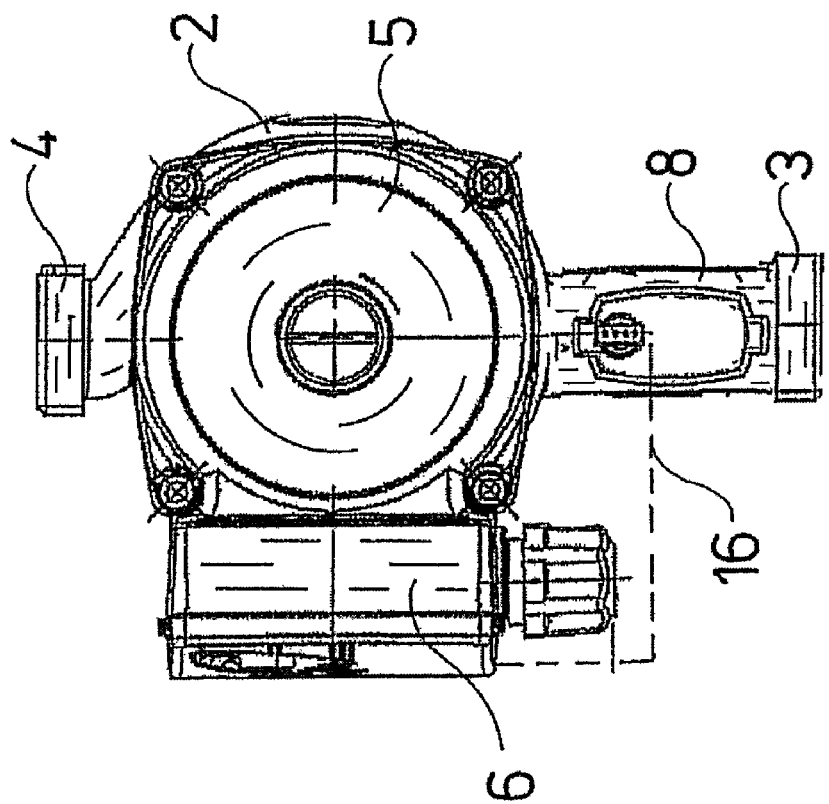
FIG. 1 a simplified schematic perspective plan view of a centrifugal pump assembly with an integrated device for viscosity detection.

The centrifugal pump assembly represented in the FIGS. 1 and 2 comprises an inline centrifugal pump 1 whose pump housing 2 has a suction-side connection 3 leading to the suction port of the pump, as well as a pressure-side connection 4 which is arranged on the same axis to this. The centrifugal pump 1 is driven by an electric motor 5, which comprises a terminal and electronics box 6, which is arranged laterally on the motor housing and in which a frequency converter is arranged, with which the motor speed may be controlled. A corresponding control 7 in the form of digital control electronics is arranged in the terminal box 6. A vortex measurement device whose construction is represented in detail by way of FIG. 3, is arranged in the pump-side suction conduit 8 connecting to the suction union 3.

A sleeve 9 is inserted into the suction conduit 8, and this sleeve comprises a body 11 which is arranged transversely to the flow direction and which forms an obstacle to the through-flow. The body 11 is arranged and designed such that counter-running vortices form therebehind in the flow direction 10 when subjected to onflow, this being the so-called Karma vortex street. A sensor body 12 is applied at a distance behind the body 11 in the flow direction for detecting these vortices, and this sensor body is held with a positive fit, sealed in a recess of the suction conduit 8, by way of an O-ring 13 and by way of an opening located therebehind in the sleeve 9 in an aligned manner. The sensor body 12 is designed as a component which may be handled in a unified manner, and in its region around which the fluid flows, comprises a differential pressure sensor 14 with which the frequency of the vortices forming behind the body 11 may be detected, as well as a temperature sensor 15 for detecting the temperature of the fluid flowing through. The sensors 14 and 15 arranged in the sensor body 12 are connected via a data lead 16 to the evaluation electronics 17 in the terminal box and electronics box 6 of the motor.

Figure 3:
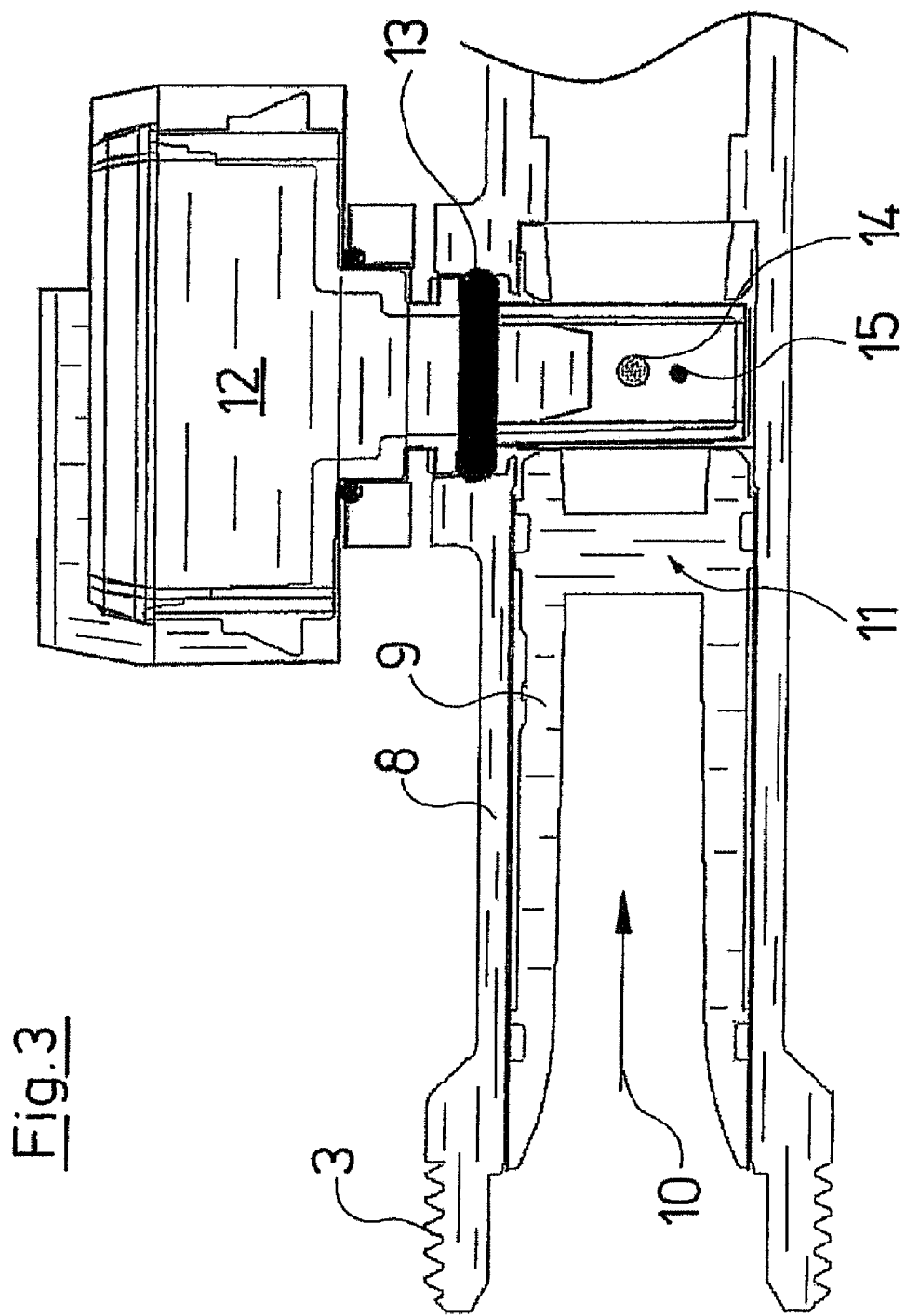
FIG. 3 is a simplified schematic section view of a conduit section with a vortex measurement device.

The measurement arrangement in the suction conduit, which is represented by way of FIG. 3, may alternatively also be arranged in any conduit section, and the evaluation electronics 17 as well as parts of the control electronics 7 do not need to form part of the pump assembly.

The above-described device functions as follows on operation:

The fluid flowing into the centrifugal pump 1 via the suction conduit 8, with an adequate flow speed, is excited at the body 11 into a vortex formation, which is detected by way of the differential pressure sensor 14 arranged at a distance therebehind and which, while taking into account the temperature determined by way of the temperature sensor 15, is led to the evaluation electronics which determine the flow speed on account of this data, as is counted as belonging to the state of the art with such vortex measurement arrangements.

The electric motor 5 of the centrifugal pump 1, may, at certain intervals or upon receiving a corresponding control command, be activated from zero or a low speed with an increasing rotational speed by way of the control electronics 7. Thereby, apart from the temperature 15, in particular the signal of the differential pressure sensor 14, is monitored in the evaluation electronics 17. As soon as this sensor produces a frequency signal, this is detected in the evaluation electronics 17. This evaluated lowermost frequency signal sets in when vortices form for the first time behind the body 11, which may be detected by the sensor 14. Since the speed at which these vortices form for the first time is dependent on the viscosity of the fluid as well as on the temperature of the fluid, one may determine the viscosity of the delivered fluid in the evaluation electronics 17 by way of comparison with previous stored values.

Figure 4:
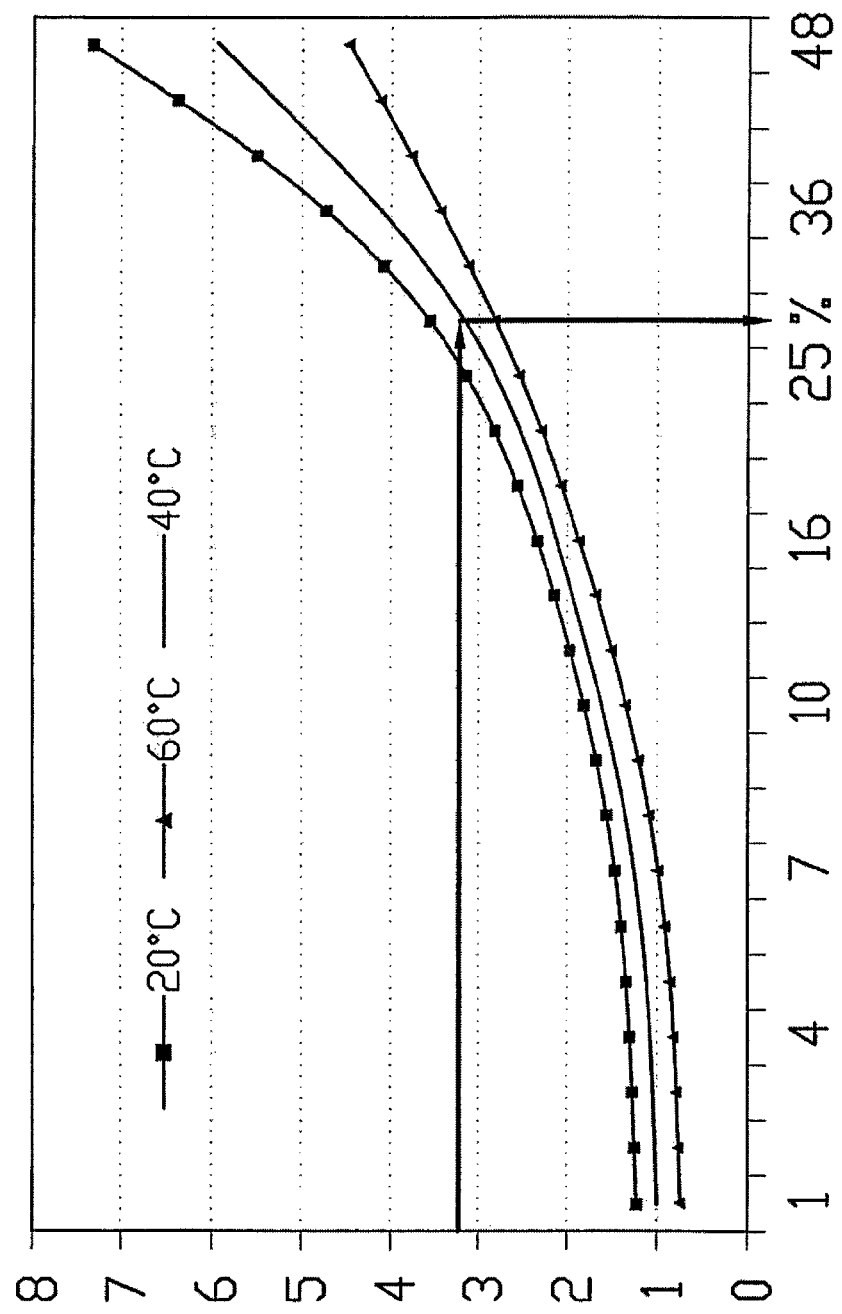
FIG. 4 is a diagram which represents the flow speed at which vortices barely just form, in dependence on the glycol content in the water, at three different temperatures.

It is represented by way of FIG. 4 as to how this first-time vortex formation behind the body 11 in the flow direction 10 sets in depending on the temperature as well as the viscosity of the fluid. The representation according to FIG. 4, however, goes one step further inasmuch as this is concerned, since it does not directly indicate the viscosity, but the percentage glycol content of a fluid based on water. Thus, by way of plotting the initial values known from the diagram according to FIG. 4 in dependence on the temperature, it is possible by way of the evaluation electronics 17 to directly determine the glycol content of the water and thus, for example, the freezing point in a direct manner by way of the previously described measurement.

The sensor body 12 which is known as such is thus given a further function by way of the control electronics 7 and the evaluation unit 17, specifically of determining the viscosity of the delivered medium or determining the glycol content of the medium or the freezing point of the medium, depending on which of the previously mentioned variables are to be used. Irrespective of this, the speed and the temperature of the medium may be detected with the sensor body 12.

Alternatively or additionally, the motor 5 may not only be activated to an increasing rotational speed from zero, but also with regard to a rotational speed dropping to zero or dropping so much, that the previously described vortex formation is barely just no longer effected, in order to determine the minimal flow speed which is necessary for determining the viscosity, at which eddies barely just continue to exist behind the body 11.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for determining the viscosity of a fluid, comprising:
    providing a body arranged in a fluid-leading channel, the body projecting into the channel and producing vortices as a result of flowing fluid;
    detecting at least one vortex forming behind the body in a flow direction of the fluid;
    determining a flow speed in the channel at which vortices form for a first time or barely just continue to exist; and
    using a value of the flow speed as a measure for a viscosity of the flowing fluid.

2. The method according to claim 1, wherein the determining of the flow speed comprises producing a flow of the flowing fluid with an increasing or decreasing speed.

3. The method according to claim 1, wherein the determining of the flow speed comprises detecting a frequency of formation of the at least one vortex behind the body in the flow direction and using the frequency to determine the flow speed.

4. The method according to claim 3, wherein the detecting of the frequency of formation of the at least one vortex is effected with a differential pressure sensor arranged in a vortex region.

5. The method according to claim 1, further comprising measuring the temperature of the flowing fluid, and utilizing the temperature measurements to determine the viscosity of the flowing fluid.

6. A method for determining the viscosity of a fluid, comprising:
    providing a body arranged in a fluid-leading channel, the body projecting into the channel and producing vortices as a result of flowing fluid, wherein the fluid comprises water and a further substance;
    detecting at least one vortex forming behind the body in a flow direction of the fluid;
    determining a flow speed in the channel at which vortices form for a first time or barely just continue to exist;
    measuring the temperature of the flowing fluid;
    utilizing the flow speed and the temperature measurements to determine a viscosity of the flowing fluid; and
    determining a content of the further substance and/or the freezing point of the fluid with the use of the viscosity of the fluid and the temperature of the fluid.

7. The method according to claim 6, wherein the further substance comprises glycol.

8. The method according to claim 1, wherein the channel is formed by a conduit, and a fluid flow in the conduit is affected by a centrifugal pump, the method further comprising activating the centrifugal pump with an increasing or decreasing rotational speed to create an increasing or decreasing fluid flow speed to thereby determine the viscosity of the fluid.

9. The method according to claim 1, wherein the channel is formed by a conduit which is impinged by a pressure source, the method further comprising providing a device for throttling or opening the conduit cross section for determining the viscosity.

10. The method according to claim 1, wherein the method is carried out by a device comprising a measurement arrangement provided for integration into a conduit (8), the measurement arrangement comprising a body (11) and a pressure sensor or differential pressure sensor (14) arranged at a distance thereto, with an electronic control and evaluation device (7, 17) configured to control a fluid flow speed in the conduit (8) and to evaluate a pressure sensor signal or a differential pressure sensor signal to determine the viscosity of the fluid in the conduit (8).

11. The method according to claim 10, wherein the measurement arrangement further comprises a temperature sensor (15).

12. The method according to claim 10, wherein the electronic control and evaluation device comprises a flow device (7) configured to change the fluid flow speed in the conduit (8), and wherein the device comprises a centrifugal pump (1) with a controllable rotational speed.

13. The method according to claim 10, wherein the conduit (8) and the measurement arrangement located therein, form a part of a centrifugal pump (1).

14. The method according to claim 10, wherein at least a part of the electronic control and evaluation device (7, 17) is arranged in a terminal box or electronics housing of a motor (5) of a centrifugal pump (1).

15. The method according to claim 10, wherein the electronic control and evaluation device comprises a flow device (7) configured for changing the fluid flow speed in the conduit (8), and wherein the flow device comprises a controllable throttle valve.

16. The method according to claim 10, wherein the electronic control and evaluation device comprises a flow device (7) configured for changing the fluid flow speed in the conduit (8).

* * * * *